United States Patent
Molinier et al.

(10) Patent No.: US 9,469,579 B2
(45) Date of Patent: Oct. 18, 2016

(54) PROCESS FOR THE PRODUCTION OF XYLENES

(71) Applicant: ExxonMobil Chemical Patents Inc., Baytown, TX (US)

(72) Inventors: Michel Molinier, Houston, TX (US); Jeffrey L. Andrews, Houston, TX (US); Timothy P. Bender, Houston, TX (US); Robert G. Tinger, Friendswood, TX (US); Dennis J. Stanley, Houston, TX (US); George J. Wagner, Tomball, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/160,507

(22) Filed: May 20, 2016

(65) Prior Publication Data

US 2016/0264495 A1    Sep. 15, 2016

Related U.S. Application Data

(63) Continuation-in-part of application No. 14/735,695, filed on Jun. 10, 2015.

(60) Provisional application No. 62/018,724, filed on Jun. 30, 2014.

(51) Int. Cl.
| | | |
|---|---|---|
| *C07C 2/66* | (2006.01) | |
| *C07C 1/20* | (2006.01) | |
| *C07C 6/12* | (2006.01) | |

(Continued)

(52) U.S. Cl.
CPC ............. *C07C 5/2767* (2013.01); *C07C 2/864* (2013.01); *C07C 5/2729* (2013.01); *C07C 6/06* (2013.01)

(58) Field of Classification Search
CPC ............. C07C 2/66; C07C 1/20; C07C 6/12; C07C 5/27
See application file for complete search history.

(56) References Cited

U.S. PATENT DOCUMENTS

| | | |
|---|---|---|
| 4,066,712 A | 1/1978 | Harris |
| 4,886,930 A | 12/1989 | Zinnen |

(Continued)

FOREIGN PATENT DOCUMENTS

| | | |
|---|---|---|
| CN | 103449956 | 12/2003 |
| WO | 2013/085681 | 7/2013 |
| WO | 2014/058550 | 4/2014 |

OTHER PUBLICATIONS

U.S. Appl. No. 62/018,724, filed Jun. 30, 2014, Molinier et al.

(Continued)

*Primary Examiner* — Thuan D Dang

(57) ABSTRACT

In a process for producing para-xylene, a toluene-containing stream is contacted with a methylating agent under conditions effective to convert toluene to xylenes and produce a methylated effluent stream. Para-xylene is recovered from the methylated effluent stream to produce a para-xylene depleted stream and part of the para-xylene depleted stream is contacted with a xylene isomerization catalyst under liquid phase isomerization conditions effective to produce a first isomerized stream, while part of the para-xylene depleted stream is contacted with a xylene isomerization catalyst under vapor phase isomerization conditions effective to produce a second isomerized stream. The first and second isomerized streams are then recycled to the para-xylene recovery step.

11 Claims, 3 Drawing Sheets

(51) Int. Cl.
*C07C 5/27* (2006.01)
*C07C 6/06* (2006.01)
*C07C 2/86* (2006.01)

(56) References Cited

U.S. PATENT DOCUMENTS

| | | |
|---|---|---|
| 4,956,522 A | 9/1990 | Zinnen |
| 5,057,643 A | 10/1991 | Zinnen |
| 5,516,956 A | 5/1996 | Abichandani et al. |
| 5,563,310 A | 10/1996 | Chang et al. |
| 5,625,103 A | 4/1997 | Abichandani et al. |
| 6,423,879 B1 | 7/2002 | Brown et al. |
| 6,504,072 B1 | 1/2003 | Brown et al. |
| 6,642,426 B1 | 11/2003 | Johnson et al. |
| 7,663,010 B2 | 2/2010 | Levin |
| 7,989,672 B2 | 8/2011 | Kinn et al. |
| 9,012,711 B2 | 4/2015 | Ou et al. |
| 2010/0168347 A1 | 7/2010 | Butler |
| 2010/0228066 A1 | 9/2010 | Kong et al. |
| 2011/0009682 A1 | 1/2011 | Matsushita et al. |
| 2011/0263918 A1 | 10/2011 | Ou et al. |
| 2011/0319688 A1 | 12/2011 | Ou |
| 2012/0316375 A1 | 12/2012 | Zheng et al. |
| 2013/0296624 A1 | 11/2013 | Iaccino et al. |
| 2014/0100402 A1 | 4/2014 | Gawlik et al. |

OTHER PUBLICATIONS

U.S. Appl. No. 62/018,726, filed Jun. 30, 2014, Molinier et al.

PROCESS FOR THE PRODUCTION OF XYLENES

CROSS REFERENCE TO RELATED APPLICATIONS

The present application is a continuation-in-part of and claims priority to and the benefit of U.S. application Ser. No. 14/735,695, filed Jun. 10, 2015, which claims priority and the benefit of U.S. Provisional Application No. 62/018,724, filed Jun. 30, 2014, which is incorporated by reference in its entirety. Related applications are U.S. application Ser. No. 14/735,753, filed Jun. 10, 2015 and U.S. application Ser. No. 14/735,531, filed Jun. 10, 2015.

FIELD OF THE INVENTION

This invention relates to a process and apparatus for the production of xylenes and particularly for the production of para-xylene.

BACKGROUND OF THE INVENTION

A major source of xylenes is catalytic reformate, which is produced by contacting petroleum naphtha with a hydrogenation/dehydrogenation catalyst on a support. The resulting reformate is a complex mixture of paraffins and $C_6$ to $C_8$ aromatics, in addition to a significant quantity of heavier aromatic hydrocarbons. After removing the light ($C_5-$) paraffinic components, the remainder of reformate is normally separated into $C_{7-}$, $C_8$, and $C_{9+}$-containing fractions using a plurality of distillation steps. Benzene can then be recovered from the $C_{7-}$-containing fraction to leave a toluene-rich fraction which is generally used to produce additional $C_8$ aromatics by toluene disproportionation and/or transalkylation with part of the $C_{9+}$-aromatics containing fraction. The $C_8$-containing fraction is fed to a xylene production loop where para-xylene is recovered, generally by adsorption or crystallization, and the resultant para-xylene depleted stream is subjected to catalytic conversion to isomerize the xylenes back towards equilibrium distribution. The resultant isomerized xylene stream can then be recycled to the para-xylene recovery unit.

Although benzene and toluene are important aromatic hydrocarbons, the demand for xylenes, particularly para-xylene, outstrips that for benzene and toluene and currently is growing at an annual rate of 5-7%. There is therefore a continuing need to develop aromatics production technologies which maximize the production of para-xylene, while minimizing the associated capital and operating costs.

SUMMARY OF THE INVENTION

According to the present invention, an improved process and apparatus for producing para-xylene, optionally together with benzene and/or ortho-xylene, has now been developed in which methylation, rather than transalkylation with $C_{9+}$ aromatics, is used to convert toluene, and optionally benzene, in a reformate or similar aromatics fraction to additional xylenes. Toluene methylation produces more para-xylene and less ethylbenzene than toluene transalkylation with $C_{9+}$ aromatics. As a result the production and operating costs of the xylenes separation section can be reduced and less costly liquid phase processes can be used for part of the xylene isomerization section.

Thus, in one aspect, the invention resides in a process for producing para-xylene, in which a feed stream comprising $C_{6+}$ aromatic hydrocarbons is separated into at least a toluene-containing stream and a $C_8$ aromatic hydrocarbon-containing stream and at least part of the toluene-containing stream is contacted with a methylating agent under conditions effective to convert toluene to xylenes and produce a methylated effluent stream. Para-xylene is recovered from the $C_8$ aromatic hydrocarbon-containing stream and the methylated effluent stream to produce at least one para-xylene depleted stream. At least part of a para-xylene depleted stream is contacted with a xylene isomerization catalyst under liquid phase conditions effective to isomerize xylenes in the para-xylene depleted stream and produce a first isomerized stream, and at least part of a para-xylene depleted stream is contacted with a xylene isomerization catalyst under vapor phase conditions effective to isomerize xylenes and dealkylate or isomerize ethylbenzene in the para-xylene depleted stream and produce a second isomerized stream. At least part of the first and second isomerized streams are then recycled to the para-xylene recovery step.

In a further aspect, the invention resides in a process for producing para-xylene, in which a feed stream comprising $C_{6+}$ aromatic hydrocarbons is separated into at least a toluene-containing stream and a $C_8$ aromatic hydrocarbon-containing stream, and at least part of the toluene-containing stream is contacted with a disproportionation catalyst under conditions effective to convert toluene to benzene and xylenes and produce a disproportionated effluent stream. At least part of the benzene in the disproportionated effluent stream is contacted with a methylating agent under conditions effective to convert benzene to toluene and xylenes and produce a methylated effluent stream. At least part of the toluene in the methylated effluent stream is recycled to the toluene disproportionation step.

Para-xylene is recovered from the $C_8$ aromatic hydrocarbon-containing stream and the disproportionated effluent stream to produce at least one para-xylene depleted stream. At least part of a para-xylene depleted stream is contacted with a xylene isomerization catalyst under liquid phase conditions effective to isomerize xylenes in the para-xylene depleted stream and produce a first isomerized stream, and at least part of a para-xylene depleted stream is contacted with a xylene isomerization catalyst under vapor phase conditions effective to isomerize xylenes and dealkylate or isomerize ethylbenzene in the para-xylene depleted stream and produce a second isomerized stream. At least part of the first and second isomerized streams are then recycled to the para-xylene recovery step.

In a further aspect, the invention resides in an apparatus for producing para-xylene comprising a catalytic reformer for producing a reformate stream comprising $C_{6+}$ aromatic hydrocarbons, a first separation system for separating the reformate stream into a $C_{7-}$ aromatic hydrocarbon-containing stream and a $C_{8+}$ aromatic hydrocarbon-containing stream, a toluene methylation unit for methylating benzene and/or toluene in the $C_{7-}$ aromatic hydrocarbon-containing stream to produce a methylated effluent stream, a second separation system for recovering para-xylene from the $C_{8+}$ aromatic hydrocarbon-containing stream and the methylated effluent stream to produce at least one para-xylene depleted stream, a liquid phase xylene isomerization unit for isomerizing xylenes in the at least one para-xylene depleted stream to produce a first isomerized stream, a vapor phase xylene isomerization unit for isomerizing xylenes and dealkylating or isomerizing ethylbenzene in the at least one para-xylene depleted stream to produce a second isomerized stream, and a recycle system for recycling at least part of the first isomerized stream and the second isomerized stream to the second separation system.

DETAILED DESCRIPTION OF THE EMBODIMENTS

Figure 1:
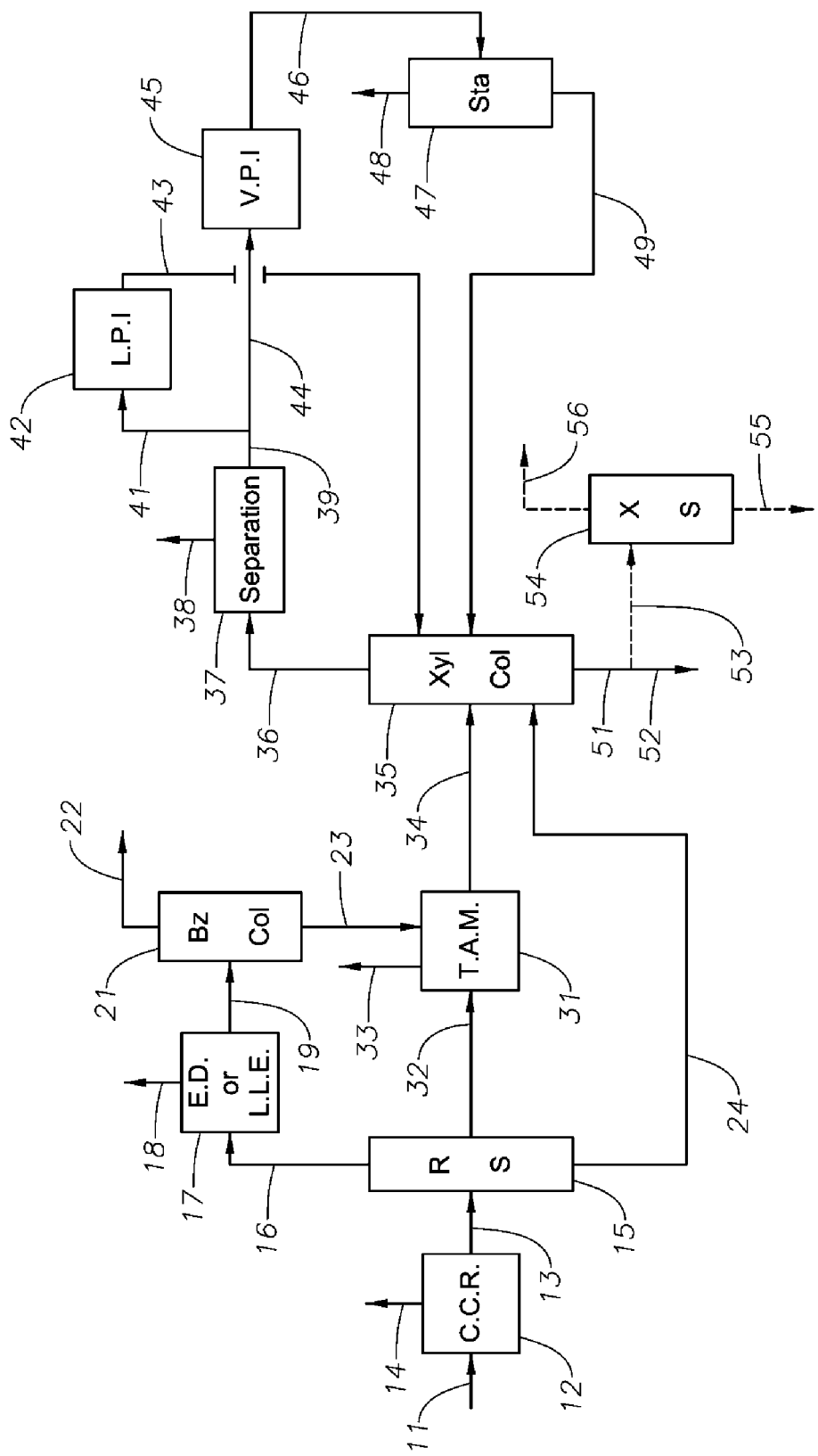
FIG. 1 is a flow diagram of a process for producing para-xylene from catalytic reformate according to a first embodiment of the invention.

The present invention describes a process and apparatus for producing para-xylene, optionally together with benzene and/or ortho-xylene, from a reformate or similar aromatics fraction in which methylation, rather than transalkylation with $C_{9+}$ aromatics, is used to convert toluene and/or benzene in the reformate fraction to additional xylenes. By adding methylation to the aromatics complex, all aromatic rings can be converted to para-xylene if benzene product is not desired. Furthermore, if benzene product is occasionally desired, an aromatics complex with a methylation unit can produce both benzene and para-xylene when benzene production is favored and produce little to no benzene when benzene production is not favored.

The feed stream to the methylation reactor may be from any source in a conventional refinery, aromatics, or steam cracking complex, such as a treated or untreated pyrolysis gasoline, reformate from a naphtha reformer, fluidized catalytic-cracked (FCC) naphtha, FCC light cycle oil (LCO), hydrocrackate, xylene isomerization product, transalkylation product, toluene disproportionation product, or any stream containing toluene and/or benzene. Alternatively, the feed stream may be a byproduct from unconventional sources such as bio-based or coal-derived feedstocks. The toluene and/or benzene containing stream may be treated upstream of the methylation reactor, such as by dealkylation, to increase the concentration of the toluene and/or benzene therein. If the feed stream is imported from an external source, such as through a pipeline, land-going vehicle, or water-going vehicle, the feed stream may be exposed to oxygen and need to be treated to remove the oxygen and/or oxygen reactive species, such as oxygenates, prior to introduction to the methylation process. Such oxygen removal treatments may include oxygen stripping, heat soaking, caustic treatment, adsorption using activated alumina and/or molecular sieves, resins, fractionation, clay treatment, or any combination thereof.

The feed stream to the methylation reactor may also contain $C_{8+}$ aromatics, which do not require pre-treating and can be converted to either benzene and/or toluene in the methylation reactor through a dealkylation reaction. Examples of $C_{8+}$ aromatics include aromatic rings having ethyl, propyl, buytl, pentyl and heavier alkyl groups. The dealkylated byproduct can then be methylated to toluene and/or xylenes.

Any method known in the art for adding methyl groups to a phenyl ring can be used in the methylation step of the present process. However, in certain preferred embodiments, the methylation step employs a highly para-selective methylation catalyst, such as that employed in U.S. Pat. Nos. 6,423,879 and 6,504,072, the entire contents of which are incorporated herein by reference. Such a catalyst comprises a molecular sieve having a Diffusion Parameter for 2,2-dimethylbutane of about 0.1-15 $sec^{-1}$, such as 0.5-10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient ($cm^2/sec$) and r is the crystal radius (cm). The required diffusion parameters can be derived from sorption measurements provided the assumption is made that the plane sheet model describes the diffusion process. Thus, for a given sorbate loading Q, the value $Q/Q_\infty$, where $Q_\infty$ is the equilibrium sorbate loading, is mathematically related to $(Dt/r^2)^{1/2}$, where t is the time (sec) required to reach the sorbate loading Q. Graphical solutions for the plane sheet model are given by J. Crank in "The Mathematics of Diffusion," Oxford University Press, Ely House, London, 1967, the entire contents of which are incorporated herein by reference.

The molecular sieve employed in the para-selective methylation process is normally a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are particularly effective for the present methylation process since the size and shape of their pores favor the production of p-xylene over the other xylene isomers. Conventional forms of these zeolites have Diffusion Parameter values in excess of the 0.1-15 $sec^{-1}$ range referred to above. However, the required diffusivity for the catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, such as at least one oxide selected from elements of Groups 2 to 4 and 13 to 16 of the Periodic Table. Most preferably, said at least one oxide modifier is selected from oxides of boron, magnesium, calcium, lanthanum, and most preferably phosphorus. In some cases, the zeolite may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier into the catalyst is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Suitable phosphorus compounds include, but are not limited to, phosphonic, phosphinous, phosphorous and phosphoric acids, salts and esters of such acids, and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours. Similar techniques known in the art can be used to incorporate other modifying oxides into the catalyst employed in the alkylation process.

In addition to the zeolite and modifying oxide, the catalyst employed in the methylation process may include one or more binder or matrix materials resistant to the temperatures and other conditions employed in the process. Such materials include active and inactive materials such as clays, silica and/or metal oxides, such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite. Preferably, the matrix material comprises silica or a kaolin clay.

The methylation catalyst used in the present process may optionally be precoked. The precoking step may be carried out by initially loading uncoked catalyst into the methylation reactor. Then, as the reaction proceeds, coke is deposited on the catalyst surface and thereafter may be controlled within a desired range, typically from about 1 to about 20 wt % and preferably from about 1 to about 5 wt %, by periodic regeneration through exposure to an oxygen-containing atmosphere at an elevated temperature. The oxygen-containing atmosphere may be sourced from air, either dried to remove a portion or all of the moisture, or hydrated to increase the moisture content of the air up to the saturation condition, or introduced neat. The oxygen-containing atmosphere may contain between 0.1 to 100 vol % of oxygen. When greater than 20.9 vol % of oxygen (the amount of oxygen in dry air) is required for the regeneration, a supplemental stream containing a higher percentage of oxygen can be mixed with air or any other stream, for example an inert containing stream such as $N_2$, Ar, He, or mixtures thereof, to provide the oxygen-containing atmosphere. When the oxygen content required for the regenerator is less than 20.9 vol %, inert gases such as $N_2$, Ar, He, or mixtures thereof may be mixed with air stream to provide the oxygen-containing atmosphere.

During the reaction, the activity or physical properties of the catalyst may be adjusted without stopping and restarting the reaction by adding fresh catalyst or catalyst that has the desired physical properties to the system. Adding catalyst with the desired activity or physical properties allows the activity or hydrodynamic performance of the catalyst to be maintained in the target range required to achieve desired performance of the reaction in the fluid bed reactor and/or regenerator. The catalyst may be introduced into any part of the system that contains catalyst, for example, the reactor, the regenerator, or any conduit connecting the reactor and regenerator. Additionally, catalyst can be withdrawn from the fluid bed system from any location that contains catalyst, for example the reactor, the regenerator, or any conduit connecting the reactor and regenerator.

Methylation of toluene in accordance with the present process can be effected with any known methylating agent, but preferred methylating agents include methanol and/or a mixture of carbon monoxide and hydrogen.

Suitable conditions for the methylation reaction include a temperature from 350 to 700° C., such as from 500 to 600° C., a pressure of from 100 and 7000 kPa absolute, a weight hourly space velocity of from 0.5 to 1000 $hr^{-1}$, and a molar ratio of toluene to methanol (in the reactor charge) of at least about 0.2, e.g., from about 0.2 to about 20. The process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in a catalyst regenerator. One example of a suitable fluidized bed process for methylating toluene includes staged injection of the methylating agent at one or more locations downstream of the toluene feed location. Such a process in described in U.S. Pat. No. 6,642,426, the entire contents of which are incorporated herein by reference.

Using the present process, toluene and/or benzene can be alkylated with methanol so as to produce para-xylene at a selectivity of at least about 75 wt % (based on total $C_8$ aromatic product) at a per-pass aromatic conversion of at least about 15 wt % and a trimethylbenzene production level less than 1 wt %. Unreacted toluene and/or benzene and methylating agent and a portion of the water by-product may be recycled to the methylation reactor and heavy byproducts routed to fuels dispositions. The $C_8$ fraction is routed to a para-xylene separation section, which typically operates by fractional crystallization or by selective adsorption or both to recover a para-xylene product stream from the alkylation effluent and leave a para-xylene-depleted stream containing mainly $C_7$ and $C_8$ hydrocarbons. Since the toluene methylation unit enhances the para-xylene content of the reformate $C_8$ fraction, the size of the para-xylene separation section can be reduced. This is a significant advantage since the para-xylene separation section is one of the most expensive processes in an aromatics complex both from a capital cost and from an operating expense perspective.

After recovery of para-xylene in the para-xylene separation section, the remaining para-xylene-depleted stream is isomerized back to equilibrium and recycled back to the para-xylene separation section. In the present process, isomerization of the para-xylene-depleted stream is conducted by both liquid phase and vapor phase isomerization units connected in parallel and operating simultaneously or alternately. Thus, toluene methylation produces a $C_8$ aromatic stream with little to no ethylbenzene, while reforming produces a $C_8$ aromatic stream with significant ethylbenzene content. The implementation in parallel of a liquid phase isomerization (low operating cost but limited ethylbenzene removal) and a vapor phase isomerization (higher operating cost but very efficient ethylbenzene removal) enables isomerization of the various $C_8$ aromatic streams to para-xylene at reduced operating costs.

Any liquid phase catalytic isomerization process known to those skilled in the art can be used in the liquid phase xylene isomerization unit, but one preferred catalytic system is described in U.S. Patent Application Publication Nos. 2011/0263918 and 2011/0319688, the entire contents of each of which are incorporated herein by reference. Suitable conditions for the liquid phase isomerization process used herein include a temperature from about 230° C. to about 300° C. and a pressure from about 1300 to about 3500 kPa selected to maintain the para-xylene-depleted stream substantially in the liquid phase. In some embodiments, the weight hourly space velocity (WHSV) may be from about 0.5 to about 10 hr$^{-1}$.

The vapor phase isomerization unit can also employ any known isomerization catalyst system, but preferably employs a catalyst system effective to convert some or all of the ethylbenzene in the para-xylene-depleted stream as well as to return the xylenes to equilibrium concentration. Ethylbenzene removal can be effected either by dealkylation to benzene, isomerization to xylenes, disproportionation to benzene and diethylbenzene, or transalkylation with toluene, xylenes, or $C_{9+}$ aromatics. One preferred vapor phase isomerization process is described in U.S. Pat. No. 5,516,956, the entire contents of which are incorporated herein by reference. Suitable conditions for the vapor phase isomerization process include a temperature of from about 660° F. and about 900° F. (350° C. to 480° C.), a pressure from about 50 to about 400 psig (446 to 2860 kPa), a WHSV of between about 3 and about 50 hr and a hydrogen to hydrocarbon molar ratio from about 0.7 to about 5.

In some embodiments, it may be desirable to add a toluene disproportionation unit upstream of the toluene methylation unit. The toluene disproportionation unit converts toluene in the reformate to benzene and xylenes, particularly para-xylene, so that the size and operating cost of the toluene methylation unit can be decreased. Although any toluene disproportionation process can be employed, it is preferred to use a process which selectively converts toluene to para-xylene. Such a process may employ a catalyst comprising a medium-pore size aluminosilicate zeolite, such as ZSM-5, which has been selectivated with silica and/or coke. In one preferred embodiment, the process may be operated so as to include an initial adjustment phase in which toluene is contacted with a silica-selectivated catalyst under conditions sufficient to increase the para-selectivity of the catalyst, followed by a steady-state phase in which toluene is contacted with the catalyst under conditions sufficient to achieve essentially constant levels of toluene conversion and para-xylene selectivity. Such a process is described in U.S. Pat. No. 5,625,103, the entire contents of which are incorporated herein by reference. Alternatively, the toluene disproportionation unit may be located downstream of the toluene methylation unit to further convert toluene unconverted by the methylation unit.

The invention will now be more particularly described with reference to the accompanying drawings.

FIG. 1 illustrates a process for producing para-xylene according to a first embodiment of the invention, in which a naphtha feedstock is supplied by line 11 to a catalytic reformer (for example, a semi-regenerative reformer, a cycle reformer or a continuous catalytic reformer) 12. The naphtha feedstock can be tailored to produce a reformate product that contains more or less benzene and/or toluene, as one skilled in the art will be able to design. The effluent from the catalytic reformer 12 is a complex mixture of aliphatic and aromatic hydrocarbons and, after removal of the $C_{5-}$ fraction in a depentanizer (not shown), the remaining $C_{6+}$ fraction is fed by line 13 to a reformate splitter 15. Hydrogen is also generated in the catalytic reformer 12 and is removed via line 14 for use in the gas phase isomerization section described below, or in various units in a refinery, or in a cyclohexane unit or any other petrochemical process if the aromatics complex is not erected next to a refinery. Alternatively, the hydrogen can be sold as export, or used in fuel, or flared.

The reformate splitter 15, which can optionally be a dividing-wall distillation column, separates the $C_{6+}$ fraction in line 13, in one embodiment, into a $C_{6-}$-containing overhead stream, a $C_7$-containing intermediate stream and a $C_{8+}$-containing bottoms stream.

The reformate splitter overhead may also contain some or all of the toluene and/or $C_8$ aromatics present in line 13 along with their non-aromatic co-boilers, depending on specific economic objectives. In another embodiment (not shown), the reformate splitter 15 separates the $C_{6+}$ fraction in line 13 into a $C_{7-}$-containing overhead stream and a $C_{8+}$-containing bottoms stream, omitting the recovery of an intermediate stream. Again, the $C_{7-}$-containing overhead stream may also contain some or all of the $C_8$ aromatics present in line 13 along with their non-aromatic co-boilers, depending on specific economic objectives.

Returning to FIG. 1, the $C_{6-}$-containing overhead stream, or the $C_{7-}$-containing overhead stream in the alternate embodiment, from the reformate splitter 15 is sent via line 16 to an extraction section 17, which can be a liquid-liquid extraction process, an extractive distillation type process or a hybrid thereof. Non-aromatics raffinate is removed from the extraction section 17 via line 18 and can be used in an olefins oligomerization or reformate alkylation unit, or as feed to a steam cracker or to the refinery gasoline pool, or as fuel. The raffinate can also be used as feed to an aromatization unit to generate additional aromatic molecules while consuming hydrogen. The aromatics product from extraction section 17 is removed via line 19 and is supplied to a benzene column 21, optionally after pretreatment with clay or a molecular sieve catalyst to remove trace olefins or other low level impurities. Entrained water is removed from the aromatics extraction product in benzene column 21 and a benzene product is collected via line 22, typically as a sidestream from the benzene column 21. The benzene column bottoms product is rich in toluene, although it may also contain some trace xylenes and heavier alkylaromatics, and is sent via line 23 to a toluene methylation section 31. Alternatively, the trace xylenes and heavier alkylaromatics can be rejected from the toluene stream by withdrawing the toluene as a bottom side-stream located at least two trays above the bottom of the benzene column. If such a toluene side-stream is desired, ideally a column supplied with a divided wall column would be used which would increase the toluene purity. The benzene in line 22 can either be recovered for sale or hydrogenation to produce cyclohexane or can be fed to the toluene methylation section 31 for additional xylenes production.

The toluene methylation section 31 also receives the $C_7$-containing intermediate stream from the reformate splitter 15 via line 32 together with a supply of methylating agent, typically methanol (not shown in FIG. 1) or dimethyl ether. It should be noted that the split between line 16 ($C_{6-}$-containing overhead steam from the reformate splitter 15) and line 32 ($C_7$-containing intermediate stream from the reformate splitter 15) can be used to effectively control the level of non-aromatics sent to the toluene methylation section 31 since non-aromatics exiting reformate splitter 15 via line 16 to the extraction section 17 will be removed via line 18. Hence additional flow through line 16 will reduce overall non-aromatics content in the feed to the toluene methylation section 31.

In the toluene methylation section 31, toluene from lines 23 and 32, optionally together with benzene in line 22 from column 21, is reacted with methanol to produce xylenes and water. In some instances, $C_8$ aromatics are also fed to the toluene methylation section 31 via lines 23 and 32, to carry out ethylbenzene dealkylation to benzene in the toluene methylation section 31, with possible subsequent benzene methylation to toluene or xylenes in said section 31.

The toluene may be routed through a toluene furnace and/or heat exchange equipment (not shown) prior to entering the toluene methylation section 31 to vaporize the toluene and heat it to the temperature required to maintain the methylation reaction, which is dependent on the type of catalyst(s) used for the methylation process. Some catalysts require the toluene to be preheated to 400° C. while other catalysts require the toluene to be preheated to 600° C. The toluene can be heated to these temperatures in process heat exchanger equipment and/or furnaces, depending on the available heat sink in the process. Toluene that is heated to high temperatures, for example in a furnace, may reach temperatures that decompose the toluene to coke or heavier hydrocarbons which can impact the heat transfer rate. This decomposition rate can be reduced by co-feeding a diluent with the toluene upstream of the heat transfer equipment, such as nitrogen, hydrogen, fuel gas, steam, or a combination thereof. The molar ratio of these diluents to toluene can vary from 0.01 to greater than 10. Toluene decomposition can also be managed using the proper metallurgy for tubes, either in the convection section or radiant section, as one skilled in the art will understand. Examples include carbon steel, stainless steel, titanium, or other alloys. Special coatings and applications may also be used to minimize toluene decomposition effects and minimize coking. Additionally, additives may be used to minimize toluene coking. The presence of oxygen and/or oxygenates in the toluene feed may exacerbate the fouling mechanism in the toluene furnace, therefore removal of oxygen and/or oxygenates upstream of the toluene furnace would improve overall furnace reliability and heat transfer efficiency.

The efficiency of the methylation reaction improves as the methylating agent, typically methanol, is broadly and widely distributed within the reactor. The methylating agent can be introduced into the fixed bed or fluid bed reactor in a number of different ways, such as via a single injection point, several injection points, or even via a sparger arrangement. The methylating agent can be dispersed into the reactor either through nozzles that are flush to the reactor vessel or through an internal distribution network. The number of nozzles flush to the reactor can be one, a few or many. Alternatively, the methylating agent can be introduced into the fixed bed or fluid bed through an internal distributor. The internal distributor may be a single injection point, a few injection points or many injection points. In the case of a few or many injection points, the distributor may contain arteries branching off of one or more common headers, and additional sub-arteries may branch off of each artery to form a network of arteries. The arteries may be designed to have a uniform diameter, either the same or different diameter as the common headers, or be tapered in various diameters and different lengths. Along each common header or arteries there may be one or several or many nozzles to introduce the methylating agent. The size and length of these nozzles may be similar or different depending on the required distribution of the methylating agent into the reactor.

The internal distributor, arteries, and nozzles may be insulated if used in a fluid bed or fixed bed reactor. The decision to insulate or not can change the metallurgical requirements, which can range from carbon steel or stainless steels to titanium or other types of alloys commonly used. The bulk temperature of the methylating fluid and the skin temperatures inside the distribution network are preferred to be below the decomposition temperature of the methylating agent, which is known to one skilled in the art. The decomposition rate of the methylating agent can be reduced by co-feeding a diluent, such as nitrogen, hydrogen, fuel gas, steam, or a combination thereof. The molar ratio of these diluents to methylating agent can vary from 0.01 to greater than 10. The preferred distribution system for a methylating agent is a fractal distributor which contains an order of magnitude number of arteries and nozzles located both radially and axially throughout the reaction zone. The fractal distribution system can be designed to introduce the methylating agent at the same or different rates axially inside the reactor. The axial distribution can also be controlled having two or more fractal distributors with rates of methylating agent controlled externally from the reactor via common engineering methods, i.e., valves, pumps, restriction orifices, etc.

The reactor and/or regenerator may be of cold-wall or hot-wall design, or a combination thereof, as one skilled in the art will be able to design. Refractories for cold-wall design should be unreactive at reactor and regenerator operating pressures and temperatures. One skilled in the art of refractory technology will be able to specify the proper refractory material.

A process control system may be designed for the reactor to control product variables such as conversion of the reactants and para-xylene selectivity by manipulating reaction variables that affect the reaction and products. Reaction variables that may be manipulated and controlled are reactor pressure, reactor temperature, reactor WHSV, methanol to toluene ratio, water to hydrocarbon ratio, inert to hydrocarbon ratio, hydrogen to hydrocarbon ratio, methanol staging and distribution, toluene staging and distribution, catalyst circulation rate, catalyst activity, catalyst selectivity, amount of coke on catalysts, amount of fresh catalyst addition, activity and selectivity of fresh catalyst addition, amount of equilibrium catalyst withdrawal, location of catalyst withdrawal, severity of catalyst regeneration and/or catalyst stripping operations, amount of benzene and/or toluene in feed to reactor, amount of benzene and/or toluene precursors in feed (such as methyl- and ethyl-benzenes), and any other variable that could affect reactor operation. The process control system may use single loop controllers that control one product variable by manipulating one or more reaction variables or a multivariable process control application that simultaneously controls and/or optimizes more than one product variable by manipulating one or more reaction variables. A combination of single loop controllers and multivariable controllers can also be used. These controllers could also manipulate reaction variables that affect downstream processes.

The process off-gas from the toluene methylation section 31 is collected by line 33 and can be used in an olefins oligomerization unit or a reformate alkylation unit, or can be sent to a steam cracker or refinery for olefins recovery, or used as fuel gas. The xylenes-containing product from the toluene methylation section 31 is fed via line 34 to a xylene distillation column 35, which also receives the $C_{8+}$ bottoms stream from the reformate splitter 15 via line 24. Since the $C_{8+}$ bottoms stream in line 24 is heavier than the toluene methylation product stream in line 34, the line 24 may be connected to a lower portion of the xylene distillation column 35 than the line 34.

Prior to the xylene distillation tower 35, the product stream from the toluene methylation section 31 may be fed through a toluene distillation tower (not shown) to recover unconverted toluene from the xylenes and heavier components. Fresh toluene may also be fed through the toluene distillation tower. The feed point to the distillation tower for product stream and fresh toluene may be the same or different as one skilled in the art will be able to determine Additionally, there may be other streams that can be fed to the distillation tower, for example a xylenes and heavier stream from a naphtha reformer, xylene isomerization unit, disproportionation unit, transalkylation unit, or any other unit that may contain toluene and heavier aromatics. The toluene from the distillation unit is typically recovered as a liquid overhead product, after condensing via conventional cooling methods such as an air fin, water cooler or process cooler, or combination thereof, either in parallel or series configuration. The toluene may also be recovered as a vapor product, either in the overhead of the distillation tower, upstream of any cooling equipment, or as a side stream from the distillation column. Likewise, the toluene can be recovered as a liquid product from one of the trays in the distillation tower, for example, 3-5 trays below the overhead of the distillation tower. This is particularly effective if the distillation tower contains a component or components lighter than toluene, for example, water or light hydrocarbons, or even dissolved oxygen, which could reduce the concentration of toluene by dilution. The distillation column to separate toluene from heavier aromatics and impurities may also be a divided wall column, with one or more than one partitions. The recovered toluene may then be recycled back to the toluene methylation section 31 and the heavier components sent downstream for further processing.

The xylene distillation column 35 is operated to produce at least one para-xylene rich $C_8$ aromatics overhead stream, which is sent via line 36 to a separation section 37, where para-xylene product is recovered via line 38. The separation unit 37 may be based on an adsorption process or a crystallization process or any combination of both, but in any case may be optimized to manage para-xylene separation from two separate streams, namely one with ~20% para-xylene content (C8 portion of the reformate), and one with preferably ≥75% para-xylene content (toluene methylation process effluent). Such optimization will result in substantial downsizing of the overall separation section 37 as well as considerable savings in utilities consumption. Such optimization may include feeding the para-enriched xylenes stream independent of equilibrium xylenes stream as described in U.S. Pat. Nos. 8,168,845; 8,529,757; 8,481,798; 8,569,564; 8,580,120; U.S. Patent Publication No. 2012/0241384; and U.S. Provisional Patent Application No. 61/946,052, the entire contents of which are incorporated herein by reference. Invariably there will be a small amount of toluene present in the xylenes feed to the para-xylene separation section 37. If a Simulated Moving Bed (SMB) Adsorption unit is used to recover para-xylene, a fraction of the toluene present in the xylenes feed will be fractionated as a "crude" toluene product, which may contain trace amounts of xylenes or water. This stream can be sent directly to the toluene methylation section 31 without any treatment to remove trace xylenes or water, since the feed to the toluene methylation section 31 generally contains water co-feed to improve methanol utilization and to suppress feed preheat coking. A combination of both adsorption process and crystallization process in separation section 37 may include a small SMB unit (not shown) and a small crystallization unit (not shown) operating in series or in parallel with the SMB unit primarily dedicated to para-xylene separation from equilibrium xylenes stream and crystallization unit primarily dedicated to para-xylene separation from the para-xylene enriched stream.

The SMB unit will contain a raffinate column, an extract column, and a finishing column. Any of these columns may be heat integrated with other parts of the SMB unit with the toluene methylation process, with another process entirely, or a combination thereof, to improve energy efficiency. The low level heat from any of these towers may be used to heat water from ambient for use in the methylation process or any other process. One skilled in the art will be able to determine the proper heat integration design to minimize energy consumption.

After recovery of the para-xylene, the remaining liquid phase para-xylene depleted effluent from the separation section 37 is collected via line 39 and can be fed in the liquid phase via line 41 to a liquid phase xylenes isomerization section 42 where xylenes are isomerized to equilibrium. The effluent from the liquid phase isomerization section 42 collected in line 43 contains close to equilibrium para-xylene (~24%) and is recycled to the xylene column 35. In other embodiments (not shown), the effluent from the liquid phase isomerization section 42 can be sent directly to separation section 37 provided the concentration of heavy aromatics produced across the liquid phase isomerization section 42 is within the specification of the separation process used in separation section 37. U.S. Pat. No. 7,989,672, the entire contents of which are incorporated herein by reference, teaches maximum allowable $C_{9+}$ aromatics concentration for a crystallization unit, which can also apply within limits to a simulated moving bed adsorption process, or hybrids of a crystallization and a simulated moving bed adsorption process.

Alternatively, the para-depleted xylenes in line 39 can be vaporized by a heater (not shown) and fed in the gas phase via line 44 to a vapor phase xylenes isomerization section 45. The effluent from the vapor phase isomerization section 45 contains close to equilibrium para-xylene (~24%) and is collected in line 46 and then fed to stabilizer column 47, where a $C_7$-containing overhead stream is removed via line 48 and the $C_{8+}$ bottoms stream is collected and fed by line 49 to the xylene distillation column 35. When the vapor phase isomerization process used in isomerization section 45 is an ethylbenzene dealkylation type, the overhead in line 48 contains benzene and some by-product toluene. When the vapor phase isomerization process used in isomerization section 45 is an ethylbenzene isomerization type, the overhead in line 48 contains little benzene and toluene by-products. In either case, benzene can be fed to the extraction section 17 and sold as a product or sent to a cyclohexane unit; benzene can also be processed in the toluene methylation section 31 for additional xylenes production. Toluene effluent from isomerization section 45 will be processed in the toluene methylation section 31 for additional xylenes production. The combined benzene/toluene stream in line 48 can be sent directly to the toluene methylation unit 31, thereby reducing fractionation costs and maximizing capital utilization.

The xylene distillation column 35 also produces a bottoms stream, which contains $C_{9+}$ hydrocarbons, mainly produced in the catalytic reformer 12, and which is collected via line 51 and sent via line 52 to sales, to solvents, to the gasoline pool, to the fuel oil pool, and/or to olefin refinery dispositions. Additional fractionation facilities (not shown) may be required to optimize the disposition of the $C_{9+}$ bottoms stream components. However, because the quantity of $C_9$ aromatics is small, the residence time of the $C_9$ aromatics in the distillation column bottoms circuit, i.e., reboiler circuit, can be very high. These $C_9$ aromatics can then polymerize or condense into higher hydrocarbon components when exposed to high temperature and a long period, which may foul the bottoms circuit or heat exchange equipment. Additives can be used to control the rate of heavy polymerization or condensation. Alternatively, another source of $C_9$ aromatics can be added to the distillation column to dilute the $C_9$ aromatics from the toluene methylation process. This additional source of $C_9$ aromatics can be introduced either continuously or in batch mode or in semi-batch mode, and purged from the system along with the toluene methylation $C_9$ aromatics, either continuously or in batch or semi-batch mode. The additional source of $C_9$ aromatics can be introduced into the distillation column at any location in the distillation column as one skilled in the art will be able to determine.

Optionally, where ortho-xylene production is desired, the operation of the xylene distillation column 35 is adjusted to allow a portion of the ortho-xylene to be collected with $C_{9+}$ hydrocarbons via line 51, and part or all of the xylene column bottoms stream 51 may be fed via line 53 to an ortho-xylene column 54. The ortho-xylene product collected in overhead line 56 of ortho-xylene column 54 will invariably contain oxygenates produced in the toluene methylation process. These oxygenates will normally be removed in an oxygenate removal process (not shown) before final ortho-xylene product is obtained. Any oxygenate removal process can be used, but a preferred process has been described in U.S. Patent Application No. 2013/0324780, the entire contents of which are incorporated herein by reference, which describes using an adsorption selective for removing phenolic compounds. Alternatively, the phenolic compounds can be effectively removed using a caustic wash application as described in U.S. Patent Application Publication No. 2012/0316375, the entire contents of which are incorporated herein by reference. The bottoms heavies from the ortho-xylene column 54 are sent via line 55 to the gasoline pool and/or fuel oil pool. If excessive ortho-xylene is produced above production needs, a portion or all of the ortho-xylene can be processed across either liquid phase isomerization section 42 or vapor phase isomerization section 45 to produce more para-xylene.

In one modification (not shown) of the process depicted in FIG. 1, the extract from section 17, containing benzene, toluene and even possibly xylenes, along with saturated water, trace olefins and/or other non-aromatic species not rejected in stream 18, can be fed directly to toluene methylation section 31 without prior separation in a benzene column Thus, there is no need to remove the water nor the olefins nor the other non-aromatics prior to feeding the stream in line 19 to the toluene methylation section 31. The benzene in stream 19 will be methylated to toluene and, the toluene will be methylated to xylenes. The non-aromatics and olefins will be cracked to light gases with some coke formation in section 31, and if section 31 is a fluid bed type reactor, the limitations on the amount of non-aromatics present is an economic decision and not limited by the process. Therefore, section 17 can be operated in a very energy efficient mode to not reject close to 100% of the non-aromatic species in stream 18. Typical energy savings across section 17 can exceed 10% of normal energy costs. Additionally, olefin removal technology is not needed and costly fractionation of benzene from toluene and heavier is avoided.

Figure 2:
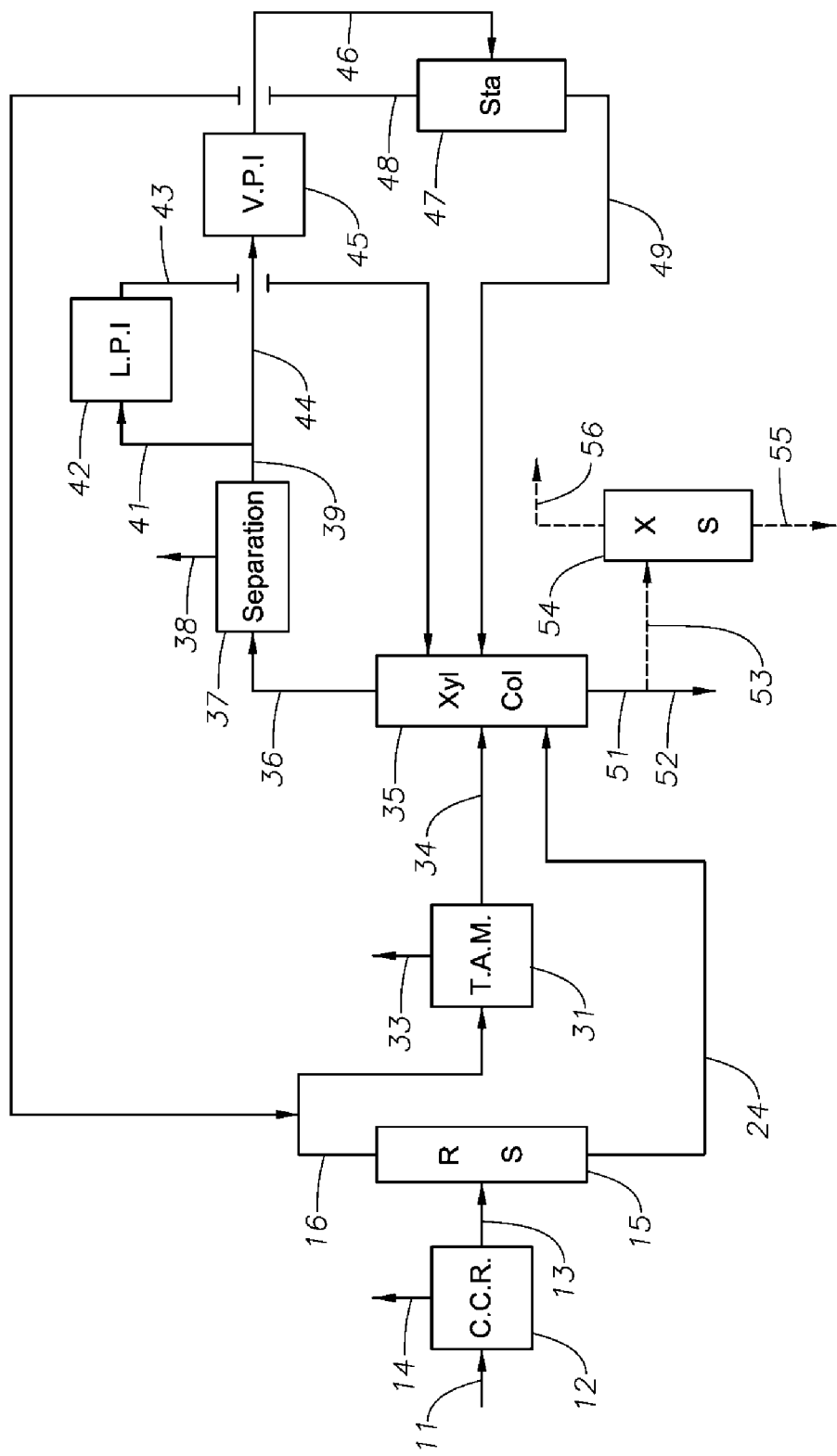
FIG. 2 is a flow diagram illustrating a process for producing para-xylene from catalytic reformate according to a modification of the first embodiment of the invention.

Another modification of the process shown in FIG. 1 is illustrated in FIG. 2, in which like reference numerals are used to indicate like components to those shown in FIG. 1. In particular, in the process shown in FIG. 2, there is no provision for non-aromatics or benzene recovery and so the extraction section 17 and the benzene column 21 of FIG. 1 are omitted. Thus, in this modification, after the $C_{5-}$ fraction of the reformer effluent is removed in a depentanizer (not shown), the effluent is fed via line 13 to a reformate splitter section 15 which separates a $C_6/C_7$-containing overhead stream from a $C_{8+}$-containing bottoms stream. The $C_6/C_7$-containing overhead stream is fed via line 16 to the toluene methylation section 31, with no benzene extraction step, and, as in the FIG. 1 embodiment, the $C_{8+}$-containing bottoms stream is fed via line 24 to the xylene distillation column 35. Another noticeable change affects the stabilizer column 47 overhead $C_6/C_7$-containing stream which is recycled via line 48 to the inlet of the toluene methylation section 31. All benzene is eventually converted to xylenes and the depicted aromatics complex generates no product benzene.

In another modification (not shown) of the process shown in FIG. 1, the product from the toluene methylation section 31 is fed to a separator drum which produces three separate phases including a liquid hydrocarbon stream, a liquid water and methanol stream, and an olefin containing off-gas stream. The separation can be carried out in one or more drums with cooling between the drums consisting of air, cooling water, or some suitable coolant stream including refrigeration. The drums can either be horizontal or vertical, or a combination thereof. Horizontal drums may contain internal baffles. The horizontal drum may contain a water boot to collect the water phase. An internal demister pad may be employed to minimize liquid carryover with the off-gas. The vertical drum may also contain the same features as the horizontal drum, as one skilled in the art will be able to design. A combination of coolers can also be used to cool the streams between the drums. The coolant exchangers may also be situated inside the separator drums. The separator drum(s) may also be combined with the quench tower to save capital.

The hydrocarbon stream recovered by the separator drum may be further processed through a distillation section, such as a toluene distillation tower and/or xylenes distillation tower 35, to separate the hydrocarbons further. The water/methanol stream is fed to a methanol stripping column to remove hydrocarbons, methanol, and other oxygenated compounds from the water. The resultant stream containing methanol, hydrocarbons and other oxygenated compounds may be recycled back to the toluene methylation section 31. The water stream may contain acids, such as formic acid, acetic acid or the like, which may reduce the pH of the stream. The water stream can be neutralized by treating with caustic, ammonia, sodium carbonate, or any other neutralizing agent known to one skilled in the art. The waste water stream can be treated at different locations; such as in the reactor effluent to the bottom of the methanol stripper, or any location between. The olefins containing stream is sent to further processing to remove contaminants before final recovery of the valuable olefin components.

In one embodiment, the toluene methylation section 31 comprises a reactor, regenerator for the catalyst, catalyst cooler, heat exchanger equipment, and gas/solids separation equipment. The reactor effluent may contain catalyst particulates, which can be separated from the reactor effluent stream using gas/solids separation equipment such as cyclones, centrifuges, gas filters, liquid filters, wash columns, sand filters, columns, tanks, settlers, or a combination thereof. This equipment may be located internal to the reactor vessel, for example a cyclone or multiple cyclones, but is preferably external to the reactor vessel. The gas/solids equipment may be located either upstream of any heat exchange equipment used to recover heat from the reactor effluent stream or downstream of the heat exchange equipment. Such heat exchange equipment includes steam generators to produce steam with pressure ranging from 10 psig to 1200 psig, or heat exchange equipment to heat a process fluid using the enthalpy from the reactor effluent stream, or a combination thereof.

Catalyst solids in the reactor effluent, which are not captured by the catalyst removal techniques discussed above, may adhere to the walls of the piping and/or the walls of the heat exchange equipment. If the latter should occur, the heat transfer rate may be reduced. Injecting a scouring media upstream of the piping and/or the heat exchange equipment may reduce the accumulation of the catalyst fines. The scouring media may be fresh, spent, or equilibrated catalyst, sand, coke, or any other solid particle that is effective at removing catalyst fines adhered to the walls. The scouring media may be injected continuously or in batches, with injection rates ranging from minutes to weeks between batch injections. Other techniques to remove the adhered catalysts fines include gas blasting with steam, nitrogen, natural gas, or recovered reactor effluent off-gas at the point of adherence, sonic pulses or mechanical vibration at different frequencies, or using special metallurgy or coatings for the piping and/or the heat exchange equipment that inhibit the adherence of fines.

Flue gas from the regenerator may also contain catalyst fines, which must be reduced for discharge into the atmosphere. These fines can be recovered from the flue gas using many different techniques, including cyclone or multiple cyclones, an Electrostatic Precipitator, a wash column, a centrifuge, or a combination thereof. The flue gas solids recovery equipment may be upstream or downstream of any process heat exchange equipment, such as a CO boiler or any other heat exchange equipment commonly used in flue gas services. The catalyst particulates recovered from the reactor effluent or the regenerator may be returned to the reaction zone, or the regenerator zone, or both, either directly or indirectly, for example, through an intermediate storage vessel, or discharged from the system. Like the catalyst fines on the reactor side, the catalyst fines on the regenerator side may adhere to equipment downstream of the regenerator and affect heat transfer. The same methods for improving heat transfer rates described above with respect to the reactor may be used for the regenerator flue gas.

Catalyst may be withdrawn from the regenerator and fed to a heat exchange device, also known as a catalyst cooler, in order to remove the heat generated in the regenerator by the combustion of coke and other hydrocarbons on the catalyst. The withdrawal of the catalyst from the regenerator may be on a continuous or intermittent basis and of varying rates. The cooled catalyst is then fed back to the regenerator. By controlling the flow of catalyst through the catalyst cooler, and/or the amount of heat removed, the temperature of the catalyst bed in the regenerator is controlled. Depending on the amount of coke to be burned in the regenerator, the catalyst cooler may operate between maximum rates and complete shutdown. The flow of catalyst withdrawal from the regenerator is controlled using a slide valve or other suitable valve for controlling the flow of solids including solids fluidized by a suitable vapor stream (aeration media) injected into the piping both in and out of the catalyst cooler. The aeration media may be air, steam, nitrogen, hydrocarbon, and/or other suitable gas which may also be injected into the catalyst cooler to ensure fluidization of the solids within the catalyst cooler, and control the heat transfer coefficient from the fluidized catalyst, thus ensuring adequate heat transfer of the hot catalyst to the cooling medium. The catalyst cooler may also be used to preheat boiler feed water, generate steam of different pressures, preheat and/or vaporize a process stream, or heat air. The catalyst cooler is typically attached to the regenerator, attached to a separate structure for support, or enclosed completely or partially (stab in) inside the regenerator vessel.

Figure 3:
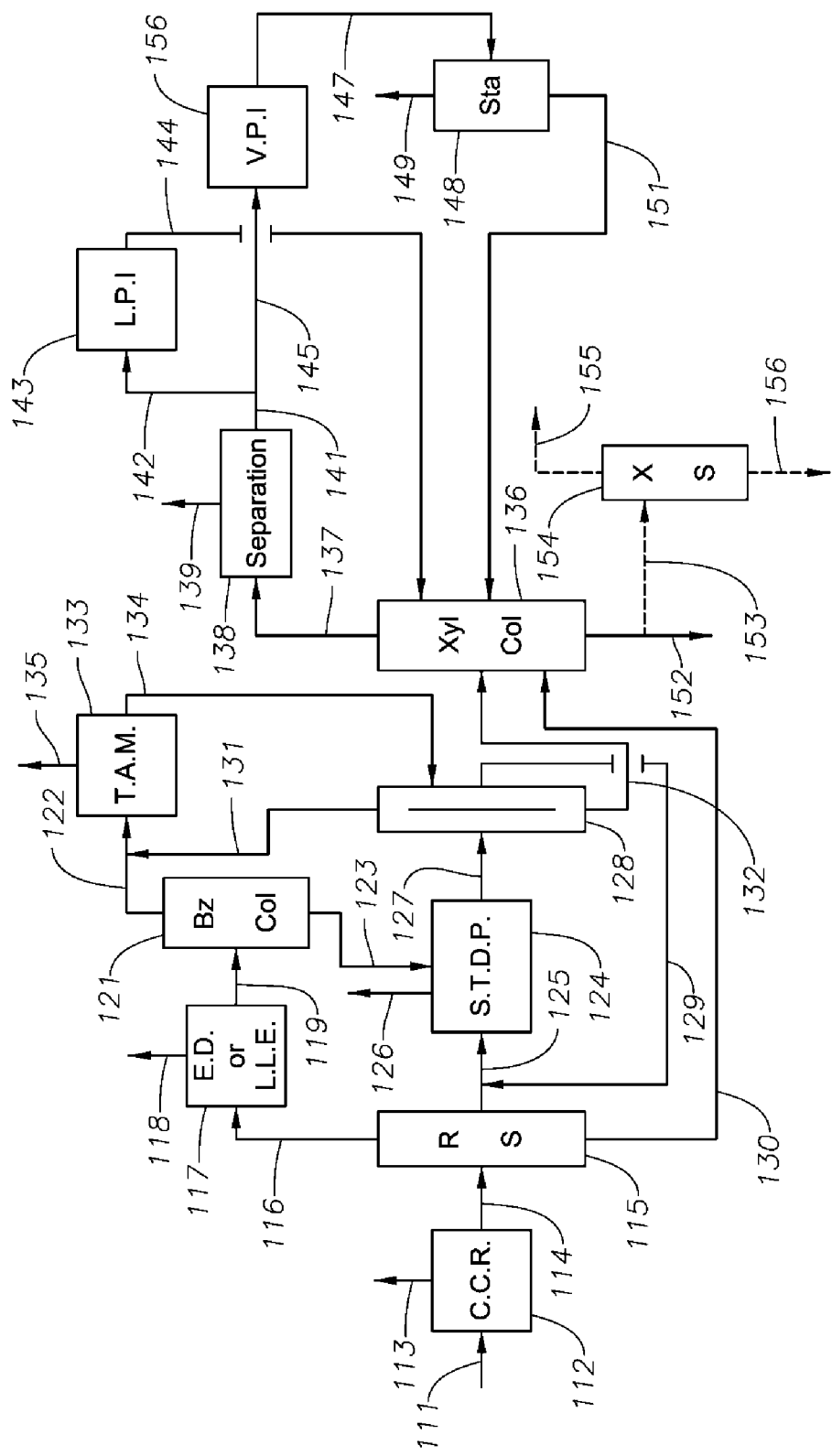
FIG. 3 is a flow diagram of a process for producing para-xylene from catalytic reformate according to a second embodiment of the invention.

FIG. 3 illustrates a process for producing para-xylene according to a second embodiment of the invention, in which a selective toluene disproportionation (STDP) section is added so as to convert at least part of the toluene in $C_7$-containing reformate fraction to xylenes thereby allowing the size of the toluene methylation section to be reduced. Thus, referring to FIG. 3, a naphtha feedstock is supplied by line 111 to a catalytic reformer (for example, a semi-regenerative reformer, a cycle reformer or a continuous catalytic reformer) 112. After removal of co-produced hydrogen via line 113 and after removal of the $C_{5-}$ fraction in a depentanizer (not shown), the remaining $C_{6+}$ effluent from the reformer 112 is fed by line 114 to a reformate splitter 115. As in the FIG. 1 embodiment, the reformate splitter 115, which can optionally be a dividing-wall distillation column, separates the $C_{6+}$ fraction in line 114 into a $C_{6-}$-containing overhead steam, a $C_7$-containing intermediate stream and a $C_{8+}$-containing bottoms stream.

The $C_{6-}$-containing overhead stream from the reformate splitter 115 is sent via line 116 to an extraction section 117, which can be a liquid-liquid extraction process, an extractive distillation type process or a hybrid thereof. Non-aromatics raffinate is removed from the extraction section 117 via line 118 leaving an aromatics product stream which is supplied via line 119 to a benzene column 121, optionally after pretreatment with clay or molecular sieve catalyst to remove trace olefins or other low level impurities. Entrained water is removed from the aromatics extraction product in benzene column 121 and a benzene-rich stream is removed via line 122, typically as a sidestream from the benzene column 121. The benzene column bottoms product is rich in toluene, although it may also contain some trace xylenes and heavier alkylaromatics, and is sent via line 123 to a selective toluene disproportionation section 124.

The selective toluene disproportionation (STDP) section 124 also receives the $C_7$-containing intermediate stream from the catalytic reformer 112 via line 125 and, as discussed above, is operated as to convert toluene selectively to benzene and para-xylene. Typically, the para-xylene concentration in the effluent from the selective toluene disproportionation section 124 comprises greater than 90 wt % of the $C_8$ component of the effluent. Off-gas from the selective toluene disproportionation section 124 is collected via line 126 and can be used as fuel gas, or as a feed to a steam cracker or may be processed in the toluene methylation section described below.

The effluent from the selective toluene disproportionation section 124 is supplied by line 127 to a BTX fractionation section 128, where at least part of the unreacted toluene is separated from the effluent and recycled to the STDP section 124 via line 129. The BTX fractionation section 128 also removes a $C_6$-containing overhead stream from the STDP effluent in line 131 to leave a $C_{8+}$ bottoms fraction which is collected and exits the BTX fractionation section 128 via line 132. As shown in FIG. 3, the BTX fractionation section 128 may be a dividing-wall distillation column.

The $C_6$-containing overhead stream in line 131 and the benzene-rich stream in line 122 are fed to a toluene methylation section 133 together with a supply of methanol (not shown). In the toluene methylation section 133, benzene from lines 122 and 131 reacts with methanol to produce toluene, xylenes and water, while any toluene present in these streams will be converted to additional xylenes. Methylated effluent is removed from the toluene methylation section 133 via line 134 and recycled to the BTX fractionation section 128, where toluene is separated from xylenes for recycle to the STDP section 124 while xylenes are collected as part of $C_{8+}$ bottoms fraction in line 132. It will therefore be seen that, in this embodiment, the toluene methylation section 133 is primarily used for benzene methylation, producing toluene and high para-xylene content xylenes. Hence the benzene column overhead stream 122 is processed in the toluene methylation section 133 while the benzene column bottoms stream 123 is processed in the STDP section 124. Alternatively, when benzene production is favored, a portion or all of the benzene-rich stream in line 122 or benzene-rich stream in line 131 can be recovered for sale or hydrogenation to produce cyclohexane.

The process off-gas from the toluene methylation section 133 is collected by line 135 and, as in the previous embodiments, can be used in an olefins oligomerization unit or a reformate alkylation unit, or can be sent to a steam cracker or refinery for olefins recovery, or used as fuel gas.

As mentioned above, the off-gas from the STDP section 124 collected by line 126 can be processed in the toluene methylation section 133, if for example toluene methylation section 133 employs a fluid bed or moving bed reactor. For a fluid bed unit, the off-gas can be used as a diluent for either benzene/toluene and/or methanol, to replace steam. Additionally, the off-gas from section 124 can be used as a purge gas in section 133, replacing steam or nitrogen or hydrogen which are conventionally used to improve fluid bed transport properties. If off-gas in line 126 contains heavier ($C_{4+}$) hydrocarbons, these will crack in section 133 to lighter olefin and paraffin products. The olefins can then be recovered in downstream equipment, such as a steam cracker.

The $C_{8+}$ bottoms fraction from the BTX fractionation section 128 is fed by line 132 to a xylene distillation column 136, which also receives the $C_{8+}$ bottoms stream from the reformate splitter 115 via line 130. Since the $C_{8+}$ bottoms stream in line 130 is heavier that the $C_{8+}$ bottoms fraction in line 132, the line 130 may be connected to a lower portion of the xylene distillation column 136 than the line 132. The xylene distillation column 136 is operated to produce at least one para-xylene rich $C_8$ aromatics overhead stream, which is sent via line 137 to a separation section 138, where para-xylene product is recovered via line 139. The separation section 138 may be based on an adsorption process or a crystallization process or any combination of both, and may be operated in the same way as the separation section 37 of FIG. 1.

After recovery of the para-xylene, the remaining liquid phase para-xylene depleted effluent from the separation section 138 is collected in line 141 and can be fed in the liquid phase via line 142 to a liquid phase xylenes isomerization section 143 where xylenes are isomerized to equilibrium. The effluent from the liquid phase isomerization section 143 collected contains close to equilibrium para-xylene (~24%) and is recycled to the xylene distillation column 136 via line 144.

Alternatively, the para-depleted xylenes in line 141 can be vaporized by a heater (not shown) and fed in the gas phase via line 145 to a vapor phase xylenes isomerization section 146. Again the effluent from the vapor phase isomerization section 146 contains close to equilibrium para-xylene (~24%) and is collected in line 147 and then fed to stabilizer column 148, where a $C_7$-containing overhead stream is removed via line 149 and the $C_{8+}$ bottoms stream is collected and fed by line 151 to the xylene distillation column 136. The stream in line 149 can be treated in the same way as the equivalent stream in line 48 of the FIG. 1 embodiment.

The xylene distillation column 136 also produces a bottoms stream, which contains $C_{9+}$ hydrocarbons, mainly produced in the catalytic reformer 112, and which is collected via line 152 and sent to sales, to solvents, to the gasoline pool, and/or to the fuel oil pool. Optionally, where ortho-xylene production is desired, the operation of the xylene distillation column 136 is adjusted to allow a portion of the ortho-xylene to be collected with $C_{9+}$ hydrocarbons via line 152, and part or all of the xylene column bottoms stream may be fed via line 153 to an ortho-xylene column 154, where ortho-xylene product is collected in overhead line 155. The bottoms heavies from the ortho-xylene column 154 are sent via line 156 to the gasoline pool and/or fuel oil pool. If excessive ortho-xylene is produced above production needs, a portion or all of the ortho-xylene can be processed across either liquid phase isomerization section 143 or vapor phase isomerization section 146 to produce more para-xylene.

The invention will now be more particularly described with reference to the following non-limiting Example.

EXAMPLE

This simulated example illustrates how the implementation of a toluene alkylation with methanol unit instead of a transalkylation unit has minimal effect on total para-xylene output of an aromatics complex based on the same feedstock as a conventional aromatics complex where xylenes are generated in the reforming and transalkylation sections. In this example, it is assumed that all xylenes will be converted to para-xylene (no ortho-xylene production). The results are shown in Table 1 below.

entitled "Xylenes Recovery with TAM (no transalkylation)" shows para-xylene production from an aromatics complex where a toluene alkylation with methanol unit has been added while the transalkylation unit has been eliminated.

As can be seen on the same feedstock and reforming section output basis, para-xylene production for a conventional aromatics complex is 560.9 kTa while para-xylene production for a complex with toluene alkylation with methanol unit and no transalkylation unit is 526.3 kTa. This means para-xylene production is essentially the same while production costs have been substantially reduced because (1) the high para-xylene content in the toluene methylation effluent considerably reduces the size of the separation section and (2) toluene methylation operation with little ethylbenzene in the effluent allows the use of liquid phase isomerization technology, which considerably reduces the overall xylenes isomerization process costs. Furthermore, para-xylene production is often favored over benzene production due to higher margins. Benzene can be fed to a transalkylation section for additional xylenes production, but this is limited by the methyl to ring ratio. However when a toluene methylation section is available, all benzene can be converted to xylenes—and further to para-xylene—if desired. Hence in the case of column #4, an additional 83.6 kTa of benzene is available for further para-xylene production.

TABLE 1

BPD 29000
kta 1245.3

| | CCR | | Xylenes_Recovery (only) | | Xylenes_Recovery and Transalkylation | | Xylenes_Recovery with TAM (no transalkylation) | |
|---|---|---|---|---|---|---|---|---|
| | Reformate | | PerCent | KTA | PerCent | KTA | PerCent | KTA |
| H2 | 4.0 | 49.8 | 3.7 | 46.4 | 3.0 | 37.6 | 3.7 | 46.4 |
| C1 | 1.3 | 16.2 | 0 | 0.0 | 0.0 | 0.0 | 0.0 | 0.0 |
| C2 | 2.1 | 26.2 | 0 | 0.0 | 0.0 | 0.0 | 0.0 | 0.0 |
| Fuel | | 0.0 | 5.0 | 62.5 | 10.0 | 127.9 | 6.5 | 80.7 |
| C3 | 2.8 | 34.9 | 0 | 0.0 | 0.0 | 0.0 | 0.0 | 0.0 |
| C4 | 3.5 | 43.6 | 0 | 0.0 | 0.0 | 0.0 | 0.0 | 0.0 |
| LPG | | 0.0 | 6.3 | 78.5 | 6.3 | 78.5 | 6.3 | 78.5 |
| C5 | 2.9 | 36.1 | 0 | 0.0 | 0.0 | 0.0 | 0.0 | 0.0 |
| C6 | 4.4 | 54.8 | 0 | 0.0 | 0.0 | 0.0 | 0.0 | 0.0 |
| C7 | 3.5 | 43.6 | 0 | 0.0 | 0.0 | 0.0 | 0.0 | 0.0 |
| C8 | 0.9 | 11.2 | 0 | 0.0 | 0.0 | 0.0 | 0.0 | 0.0 |
| Raffinate | | 0.0 | 11.7 | 145.7 | 11.7 | 145.7 | 11.7 | 145.7 |
| Bz | 3.5 | 43.6 | 6.7 | 83.6 | 15.7 | 195.7 | 6.7 | 83.6 |
| Tol | 18.0 | 224.2 | 0 | 0.0 | 0.0 | 0.0 | 0.0 | 0.0 |
| Xyl | 24.0 | 298.9 | 0 | 0.0 | 0.0 | 0.0 | 0.0 | 0.0 |
| EB | 4.8 | 59.8 | 0 | 0.0 | 0.0 | 00 | 0.0 | 0.0 |
| Px | | 0.0 | 23.0 | 286.9 | 45.0 | 560.9 | 42.3 | 526.3 |
| $A_9$ | 18.0 | 224.2 | 0 | 0.0 | 0.0 | 0.0 | 0.0 | 0.0 |
| $A_{9/10}+$ | 4.9 | 61.0 | 0 | 0.0 | 0.0 | 0.0 | 0.0 | 0.0 |
| $A_{11}+$ (FO) | 1.4 | 17.4 | 1.4 | 17.4 | 1.4 | 17.4 | 3.0 | 37.3 |
| Mogas | | 0.0 | 42.1 | 524.3 | 6.8 | 84.9 | 24.1 | 300.1 |
| MeOH | 0 | 0.0 | 0.0 | 0.0 | 0.0 | 0.0 | -9.4 | -116.9 |
| Water | | | | | | | 5.1 | 63.6 |

In Table 1, each aromatics complex employs the same feedstock (1245.3 kTa naphthas) qualitatively and quantitatively. Furthermore the reforming section provides the same product slate in all cases, the product slate being listed in column #1 entitled "CCR Reformate". Column #2 entitled "Xylenes Recovery (only)" shows para-xylene production if only reformer xylenes are recovered (no transalkylation unit). Column #3 entitled "Xylenes Recovery and Transalkylation" shows para-xylene production in a conventional aromatics complex, where a transalkylation unit has been added to produce additional xylenes. Column #4

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing para-xylene, the process comprising:

(a) separating a feed stream comprising $C_{6+}$ aromatic hydrocarbons into at least a toluene-containing stream and a $C_8$ aromatic hydrocarbon-containing stream;

(b) contacting at least part of the toluene-containing stream from step (a) with a disproportionation catalyst under conditions effective to convert toluene and produce a disproportionated effluent stream containing benzene and xylenes;

(c) separating the disproportionated effluent stream from step (b) into a benzene stream and a first xylenes stream;

(d) contacting at least part of the benzene stream from step (c) with a methylating agent under conditions effective to convert benzene and produce a methylated effluent stream containing toluene and xylenes;

(e) separating the methylated effluent stream from step (d) into a toluene stream and a second xylenes stream;

(f) recycling at least part of the toluene stream from step (e) to the disproportionation step (b);

(g) recovering para-xylene from the $C_8$ aromatic hydrocarbon-containing stream from step (a), the first xylene stream from step (c), and the second xylenes stream from step (e) to produce at least one para-xylene depleted stream;

(h) contacting at least part of the at least one para-xylene depleted stream from step (g) with a xylene isomerization catalyst under liquid phase conditions effective to isomerize xylenes in the para-xylene depleted stream and produce a first isomerized stream;

(i) contacting at least part of the at least one para-xylene depleted stream from step (g) with a xylene isomerization catalyst under vapor phase conditions effective to isomerize xylenes and dealkylate or isomerize ethylbenzene in the para-xylene depleted stream and produce a second isomerized stream; and (j) recycling at least part of the first isomerized stream from step (h) and second isomerized stream from step (i) to the para-xylene recovery step (g).

2. The process of claim 1, wherein the feed stream in (a) comprises a mixture of $C_{6+}$ aromatic and aliphatic hydrocarbons produced by removing $C_{5-}$ hydrocarbons from a reformate stream.

3. The process of claim 1, wherein the separating (a) also produces a benzene-containing stream.

4. The process of claim 1, wherein the separating (a) is conducted by a dividing wall distillation column.

5. The process of claim 3, wherein at least part of the benzene-containing stream from step (a) is supplied to the disproportionation step (b).

6. The process of claim 1, wherein the methylating agent comprises methanol.

7. The process of claim 1, wherein methylation step (c) is conducted in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa).

8. The process of claim 7, wherein said porous crystalline material comprises ZSM-5 which has undergone prior treatment with steam at a temperature of at least 950° C.

9. The process of claim 1, wherein the disproportionation catalyst comprises ZSM-5 which has been selectivated with a silicon compound.

10. The process of claim 1, wherein the separating step (c) is conducted by a dividing wall distillation column which separates the disproportionated effluent stream into a benzene stream, at least part of which is supplied to the methylation step (d), and a first xylenes stream, at least part of which is supplied to the para-xylene recovery step (g).

11. The process of claim 1 and further comprising:

(k) recovering ortho-xylene from at least one of the $C_8$ aromatic hydrocarbon-containing stream from step (a) and the second xylenes stream from step (e).

* * * * *